(12) United States Patent
Halpern et al.

(10) Patent No.: US 10,674,914 B1
(45) Date of Patent: Jun. 9, 2020

(54) WIRELESS NEURAL INTERFACE SYSTEM

(71) Applicant: Modular Bionics Inc., Santa Ana, CA (US)

(72) Inventors: Ian Loren Halpern, San Francisco, CA (US); Mark William Merlo, Santa Ana, CA (US)

(73) Assignee: Modular Bionics Inc., Berkeley, CA (US)

( * ) Notice: Subject to any disclaimer, the term of this patent is extended or adjusted under 35 U.S.C. 154(b) by 793 days.

(21) Appl. No.: 15/192,905

(22) Filed: Jun. 24, 2016

Related U.S. Application Data

(60) Provisional application No. 62/183,867, filed on Jun. 24, 2015.

(51) Int. Cl.
| | |
|---|---|
| *A61B 5/00* | (2006.01) |
| *A61B 5/04* | (2006.01) |
| *H04B 1/7163* | (2011.01) |
| *A61N 1/36* | (2006.01) |
| *A61N 1/372* | (2006.01) |

(52) U.S. Cl.
CPC ........ *A61B 5/0031* (2013.01); *A61B 5/04001* (2013.01); *A61B 5/686* (2013.01); *A61N 1/36139* (2013.01); *A61N 1/37229* (2013.01); *H04B 1/7163* (2013.01)

(58) Field of Classification Search
CPC ... A61B 5/0031; A61B 5/04001; A61B 5/686; A61N 1/37229; A61N 1/36139; H04B 1/7163; H01Q 13/10; H01Q 1/245; H01Q 1/526
See application file for complete search history.

(56) References Cited

U.S. PATENT DOCUMENTS

| | | |
|---|---|---|
| 4,151,365 A | 2/1979 | Fischell et al. |
| 4,154,228 A | 5/1979 | Feldstein et al. |
| 4,207,903 A | 6/1980 | O'Neill |
| 4,213,465 A | 7/1980 | Renheim |
| 4,441,498 A | 4/1984 | Nordling |
| 4,461,304 A | 7/1984 | Kuperstein |

(Continued)

FOREIGN PATENT DOCUMENTS

| | | |
|---|---|---|
| EP | 1985579 | 10/2008 |
| WO | WO 2010/138228 | 12/2010 |
| WO | WO 2013/096873 | 6/2013 |

OTHER PUBLICATIONS

Barna, James S., et al., "A New Multielectrode Array for the Simultaneous Recording of Field Potentials and Unit Activity", Electroencephalography and Clinical Neurophysiology 1981, 52: pp. 494-496.

(Continued)

*Primary Examiner* — Eric J Messersmith
(74) *Attorney, Agent, or Firm* — Knobbe, Martens, Olson & Bear, LLP

(57) ABSTRACT

A device system and method for wirelessly communicating through tissue is provided. The device system comprises an implanted device with an array of antennas aligned with a tandem device with an array of antennas outside of the body. The two devices wirelessly communicate in a bi-directional manner. The implanted device can act as a physiological sensor and stimulator, and the external device can act as a controller and relay. Such configurations allow for a range of uses within research and clinical settings.

20 Claims, 6 Drawing Sheets

(56) References Cited

U.S. PATENT DOCUMENTS

| | | | |
|---|---|---|---|
| 4,573,481 A | 3/1986 | Bullara | |
| 4,640,983 A | 2/1987 | Comte | |
| 4,920,979 A | 5/1990 | Bullara | |
| 4,964,414 A | 10/1990 | Handa et al. | |
| 5,215,088 A | 6/1993 | Normann et al. | |
| 5,361,760 A | 11/1994 | Normann et al. | |
| 5,645,586 A | 7/1997 | Meltzer | |
| 5,938,689 A | 8/1999 | Fischell et al. | |
| 6,002,957 A | 12/1999 | Finneran | |
| 6,009,350 A | 12/1999 | Renken | |
| 6,135,968 A | 10/2000 | Brounstein | |
| 6,215,454 B1 * | 4/2001 | Tran | H01Q 1/243 343/702 |
| 6,304,785 B1 | 10/2001 | McCreery et al. | |
| 6,447,530 B1 | 9/2002 | Ostrovsky et al. | |
| 6,456,256 B1 | 9/2002 | Amundson et al. | |
| 6,560,479 B2 | 5/2003 | van Drongelen | |
| 6,705,900 B2 | 3/2004 | Sommer et al. | |
| 6,719,582 B1 | 4/2004 | Swanson | |
| 6,748,260 B2 | 6/2004 | Au et al. | |
| 6,829,498 B2 | 12/2004 | Kipke et al. | |
| 6,921,295 B2 | 7/2005 | Sommer et al. | |
| 6,924,773 B1 * | 8/2005 | Paratte | H01Q 7/04 343/728 |
| 6,965,794 B2 | 11/2005 | Brody | |
| 7,006,859 B1 | 2/2006 | Osorio et al. | |
| 7,010,356 B2 | 3/2006 | Jog et al. | |
| 7,149,578 B2 | 12/2006 | Edvardsson | |
| 7,162,310 B2 | 1/2007 | Doan | |
| 7,203,548 B2 | 4/2007 | Whitehurst et al. | |
| 7,212,851 B2 | 5/2007 | Donoghue et al. | |
| 7,299,089 B2 | 11/2007 | Wolf et al. | |
| 7,343,205 B1 | 3/2008 | Pianca et al. | |
| 7,460,904 B2 | 12/2008 | Deadwyler et al. | |
| 7,548,775 B2 | 6/2009 | Kipke et al. | |
| 7,551,951 B1 | 6/2009 | Osorio et al. | |
| 7,729,758 B2 | 6/2010 | Haller et al. | |
| 7,751,877 B2 | 7/2010 | Flaherty et al. | |
| 7,805,175 B2 | 9/2010 | Lin et al. | |
| 7,991,475 B1 | 8/2011 | Tang et al. | |
| 8,024,022 B2 | 9/2011 | Schulman et al. | |
| 8,027,735 B1 | 9/2011 | Tzivskos et al. | |
| 8,086,322 B2 | 12/2011 | Schouenborg | |
| 8,090,448 B2 | 1/2012 | Greenberg et al. | |
| 8,112,160 B2 | 2/2012 | Foster | |
| 8,160,696 B2 | 4/2012 | Bendett et al. | |
| 8,224,459 B1 | 7/2012 | Pianca et al. | |
| 8,255,061 B2 | 8/2012 | Perlin et al. | |
| 8,498,694 B2 | 7/2013 | McGuire, Jr. et al. | |
| 8,774,937 B2 | 7/2014 | Mercanzini et al. | |
| 8,958,868 B2 | 2/2015 | Ghovanloo et al. | |
| 9,095,267 B2 | 8/2015 | Halpern et al. | |
| 9,240,630 B2 | 1/2016 | Joshi | |
| 10,086,192 B2 | 10/2018 | Halpern et al. | |
| 2004/0082875 A1 | 4/2004 | Donoghue et al. | |
| 2004/0199235 A1 | 10/2004 | Younis | |
| 2005/0021117 A1 | 1/2005 | He et al. | |
| 2006/0173263 A1 | 8/2006 | He et al. | |
| 2006/0178655 A1 | 8/2006 | Santini, Jr. et al. | |
| 2006/0276882 A1 | 12/2006 | Case et al. | |
| 2007/0191906 A1 | 8/2007 | Iyer et al. | |
| 2008/0044449 A1 | 2/2008 | McKay | |
| 2008/0177364 A1 | 7/2008 | Bolea et al. | |
| 2008/0249443 A1 | 10/2008 | Avitable et al. | |
| 2009/0099441 A1 | 4/2009 | Giszter et al. | |
| 2009/0112278 A1 | 4/2009 | Wingeier et al. | |
| 2009/0157141 A1 | 6/2009 | Chiao et al. | |
| 2009/0177144 A1 | 7/2009 | Masmanidis et al. | |
| 2010/0023021 A1 | 1/2010 | Flaherty | |
| 2010/0178810 A2 | 7/2010 | Aarts et al. | |
| 2010/0198281 A1 | 8/2010 | Chang et al. | |
| 2010/0292759 A1 | 11/2010 | Hahn et al. | |
| 2011/0144467 A1 | 6/2011 | Yao et al. | |
| 2011/0144639 A1 | 6/2011 | Govari | |
| 2011/0288619 A1 | 11/2011 | Pianca | |
| 2012/0083719 A1 | 4/2012 | Mishelevich | |
| 2012/0123289 A1 | 5/2012 | Sorenson et al. | |
| 2012/0203129 A1 | 8/2012 | Rennaker | |
| 2012/0302856 A1 | 11/2012 | Chang et al. | |
| 2013/0002519 A1 * | 1/2013 | Camacho | G06F 1/1616 343/905 |
| 2013/0172717 A1 | 7/2013 | Halpern et al. | |
| 2014/0094674 A1 | 4/2014 | Nurmikko et al. | |
| 2014/0213891 A1 | 7/2014 | Gilgunn et al. | |
| 2015/0335883 A1 | 11/2015 | Halpern et al. | |
| 2018/0008819 A1 | 1/2018 | Halpern et al. | |

OTHER PUBLICATIONS

International Search Report dated Apr. 4, 2013 for PCT App. No. PCT/US2012/071429 in 8 pages.
Jellema et al. "A slim needle-shaped multiwire microelectrode for intracerebral recording." J. Neurosci. Methods, 40 (1991) 203-209.
Karmos, George, et al., "A New Multielectrode for Chronic Recording of Intracortical Field Potentials in Cats", Physiology & Behavior, 1982, vol. 29, pp. 567-570.
Nicolelis, Miguel A.L., "Methods for Neural Ensemble Recordings", CRC Press LLC, 1999, pp. 5-12 in 10 pages.
Plexon Neurotechnology Research Systems, V-Probe Technical Guide 8, 16, 24 and 32 Channels (2013) in 14 pages.
Ulbert, Dr. Istvan, "Investigation of the evoked and spontaneous intracortical electrical activity with multielectrodes in humans", Semmelweis University Doctoral School, Neurosciences, Budapest, 2001, in 101 pages.
Ulbert, Istvan, "Multiple channel microelectrode system for human epilepsy research", IEEE, 2006, pp. 222-225.
Ulbert, Istvan, et al., "In vivo laminar electrophysiology co-registered with histology in the hippocampus of patients with temporal lobe epilepsy", Experimental Neurology, 187 (2004), pp. 310-318.
Ulbert, Istvan, et al., "Multiple microelectrode-recording system for human intracortical applications", Journal of Neuroscience Methods, 106 (2001) 69-79.

\* cited by examiner

WIRELESS NEURAL INTERFACE SYSTEM

REFERENCE TO RELATED APPLICATIONS

This application claims the benefit as a nonprovisional application of U.S. Prov. App. No. 62/183,867 filed on Jun. 24, 2015, which is hereby incorporated by reference in its entirety.

STATEMENT REGARDING FEDERALLY SPONSORED R&D

This invention was made with government support under DoD Contract/Federal Identifier Number W911NF-15-P-0031 awarded by the Department of Defense of the United States of America. The government may have certain rights in the invention.

BACKGROUND

Some aspects of the present invention relates generally to an implanted wireless system that interfaces with nervous systems. More particularly, some embodiments of the invention relates to device systems that can be implanted to monitor or stimulate the nervous system upon the desired research or clinical purpose.

SUMMARY

Disclosed herein is a device system capable of transmitting wireless signals through tissue. The device system can include in some embodiments housings that are transparent to electromagnetic radiation. The device system can also include shielding adjacent antennas. The device system can also include a locating element that aligns an external device with an implanted device. Also, the device system can include housings that are partially transparent to electromagnetic radiation. In some embodiments, an antenna array includes two or more antennas. In still other embodiments, a device is operably connected to a neural probe. In some embodiments, a worn device can relay information wirelessly to another device. In other embodiments, the wirelessly transmitted information can include neural signals, heart rhythms, muscle firing signals, images, and video. In some embodiments, also disclosed herein is a neural interface. The neural interface can include a housing configured to be implanted at a location in a patient under a skull and proximate neural tissue; a first antenna within the housing and configured to transmit neural data wirelessly to an external device; and a second antenna within the housing and configured to transmit neural data wirelessly to an external device. In some embodiments, the first antenna and the second antenna transmit the neural data on the same or an overlapping frequency spectrum. The housing can include shielding partially surrounding the first antenna and second antenna. The housing can also include one, two, or more shielding-free windows that allow the first antenna and the second antenna to allow wireless transmission at angles between about 90 degrees and about 180 degrees with respect to a long axis of the window. In some embodiments, the neural interface can also include a third antenna. The third antenna can be unshielded. In some embodiments, the third antenna transmits data on a frequency spectrum different from (not overlapping with) that of the first antenna and the second antenna. In some embodiments, the first antenna and the second antenna are spaced apart and separated by a wall. In some embodiments with three or more antennas, each antenna can be spaced apart by one or more walls. The wall can be dynamically movable. The shielding can extend laterally in one or more directions beyond the first antenna and the second antenna. The shielding can extend laterally by a distance of between about 0.1 mm and about 10 mm. There can be an air gap between the one or more windows and the antennas. The first antenna and the second antenna can transmit the neural data via an ultra-wideband protocol. The neural interface can also include a third antenna and a fourth antenna forming a pair of antennas. The first antenna and the second antenna can be configured to record data, and the third and fourth antennas are configured to send or receive stimulation commands. The first, second, third, and fourth antennas can be part of a closed-loop control system. The neural interface can also include a first antenna array and a second antenna array. The housing can also include a processor configured to compare the frequency and/or modulation of a signal of communication of the first antenna array and the second antenna array. In some embodiments, the first antenna and the second antenna are oriented such that the first antenna can include a first dead zone comprising a first non-transmissible or attenuated volume within the housing and the second antenna includes a second dead zone comprising a second non-transmissible or attenuated volume within the housing. The first volume and the second volume can overlap by at least about 10%, 20%, 30%, 40%, 50%, 60%, 70%, 80%, 90%, or more. In some embodiments, each antenna or pair of antennas could be enclosed in its own discrete housing.

DETAILED DESCRIPTION

Figure 1:
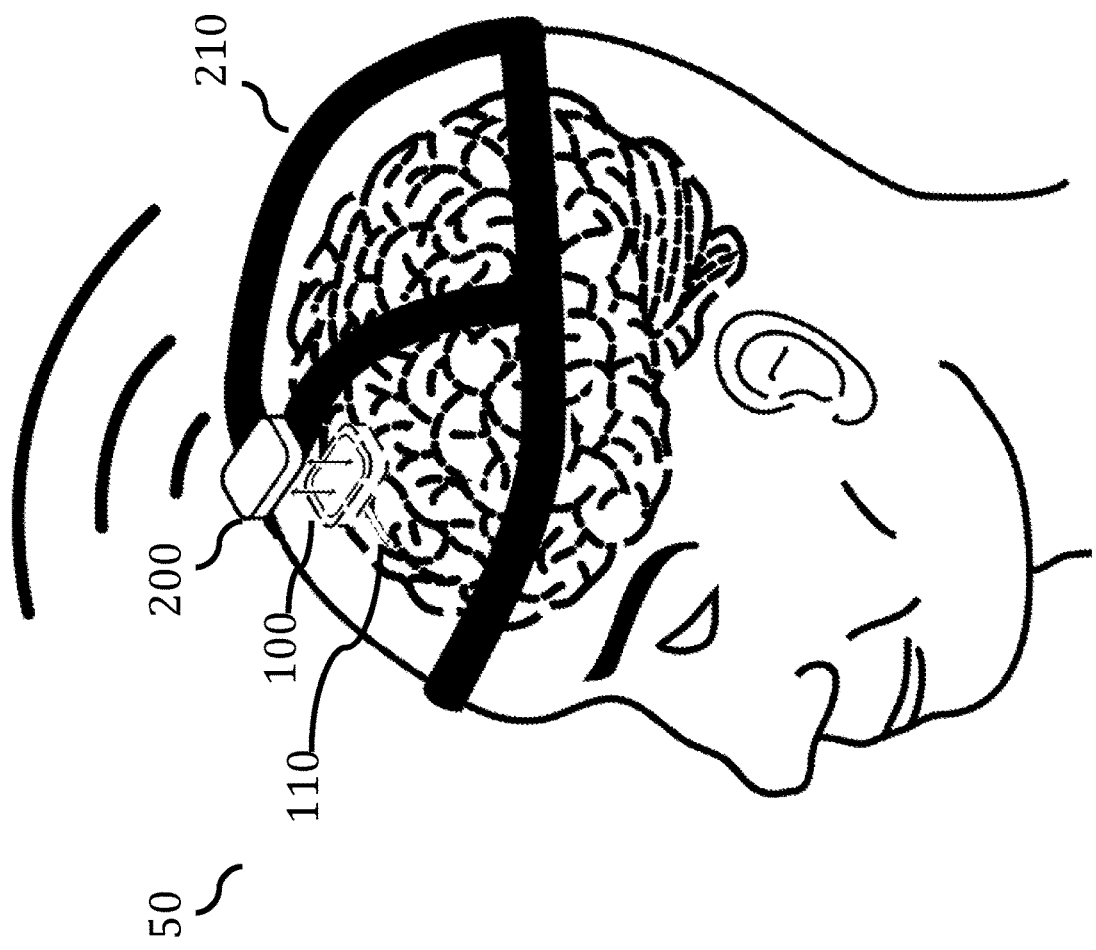
FIG. 1 shows a cross sectional view of an implanted device wirelessly communicating through tissue with an external device via antenna arrays, according to some embodiments.

Biological sensors are implanted within the bodies of animals and humans to study, record, stimulate, and treat various anatomies. Typically, this occurs within animal research of a variety of fields (e.g. neurological disorders and basic nervous system function) as well as clinical diagnosis and therapy (e.g., epilepsy).

Biological sensors are implanted for a variety of reasons, including wirelessly transmitting signals into and out of the body, through a variety of methods including radio frequency, ultrasonic, and optical transmissions. Radio frequency communication is the most pervasive form of wirelessly communicating with devices implanted within the body. It is advantageous to transmit large amounts of data into or out of the body, some non-limiting examples of this need is the recording of neurons or muscle cell firing, ion channel activity, or the sending of specific commands for stimulation or ablation. The firing of a neuron produces a distinct voltage signature over time that requires a detailed analog recording to identify. These analog recordings over long periods of time require large amounts of data to be recorded and transmitted. Transmitting at a high total data rate out of the body is advantageous as it increases the number of neuron firing events that can be identified over time.

Unfortunately, wireless transmissions are attenuated by tissue, limiting the amount of data transmitted between an implanted device and external devices. Attempts to work around this challenge are problematic and include increasing the number of implanted devices, as well as reducing tissue thicknesses to reduce signal attenuation. Reducing tissue thicknesses is time consuming during surgery and damaging or irreversible for most organisms. Increasing the number of implanted devices has proven difficult due to wireless transmissions of individual implants disrupting one another. Increasing the number of implants also increases the invasiveness of the procedure and device, increasing the risk of unsuccessful results for the implant due to infection or other surgical complications. Another significant challenge for implanted devices is providing them with power. Powering a dispersed network of implants provides many additional challenges to a device system, and connecting nodes of an implant network with cables to a single power source increases the difficulty and delicacy of implantation and aides the spread of infection from one area to another within a body. Alignment of external components with implanted antennas can also be challenging. These limitations prevent the implantation of wireless chronic neural interfaces in a wide variety of situations. This reduces the amount of data acquired, limiting the study of anatomy, and ultimately limits current and future therapies.

Accordingly, in some embodiments, disclosed herein is a wireless device system that increases the amount of data that can be transmitted into and out of the body within a compact device system. In some embodiments, the system may have one or more antennas operating on the same or overlapping frequency spectrum arranged in a shielded array to prevent interference with one another while increasing the total amount of data transmitted into and out of the body. It can also be advantageous to place arrays in the body in areas with thinner tissue; in one embodiment, this may be the scalp. In some embodiments, the antenna arrays may be configured with at least one other antenna operating on another frequency spectrum. As an example, this would enable one frequency for communicating with basic functions of an implanted device and another frequency spectrum for transmitting large amounts of information into and out of the body.

In some embodiments, tissue can be altered to increase the strength or reduce attenuation of wireless communication between devices. In other embodiments, tissue can be altered for positioning of a device that increases the strength or reduces attenuation of wireless communication with another device. In some embodiments, the tissue is a component of the wireless device as it alters the performance based on its thickness and density. The wireless device system's performance is affected by its integration with tissue. The tissue thickness, alignment of implanted and external antennas and the distance between implanted and external antennas, contributes to reliable communication and electromagnetic radiation emitted through tissue not contained by the device system. Designing the wireless device system for specific tissue thicknesses and anatomical locations can increase the system performance, and limits the electromagnetic radiation emitted through tissue outside the body. Limiting the electromagnetic radiation emitted through tissue outside the body and the device system can in some cases increase safety, reduces the possibility of interference with other wireless devices, and satisfies the requirements of regulatory organizations. In some embodiments, the system can be designed and configured for head tissue thicknesses of 5 mm to 25 mm, such as no more than about 6 mm, 7 mm, 8 mm, 9 mm, 10 mm, 11 mm, 12 mm, 13 mm, 14, mm, 15 mm, 17 mm, 19 mm, 21 mm, or 24 mm. In still other embodiments, the system can be designed and configured for tissue thicknesses of 1 mm to 5 mm, such as no more than about 2 mm, 3 mm, or 4 mm. In some other embodiments, the system can be designed for tissue thicknesses of 25 mm to 45 mm, such as no more than about 28 mm, 32 mm, 36 mm, 40 mm, or 44 mm.

In other embodiments, the shielding extends one, two, or more directions, such as outwardly (e.g., laterally, radially, and/or horizontally) beyond the side walls of one, two, or more antennas by a distance (shown as distance between arrows at 320 of FIG. 1B) of about 0.1 mm to about 10 mm, such as no more than about 0.25 mm, 0.3 mm, 0.5 mm, 1 mm, 3 mm, 5 mm, 7 mm, or 9 mm. In other embodiments, device system 100 and device system 200 each have only a single antenna. In still other embodiments, shielding extends beyond the single antenna by a distance of 0.1 mm to 10 mm, such as no more than about 0.25 mm, 0.3 mm, 0.5 mm, 1 mm, 3 mm, 5 mm, 7 mm, or 9 mm.

A configuration placing at least one, two, or more antennas away from shielding can be also advantageous in some embodiments as it allows the animal or person to move while maintaining communication with external devices. In some embodiments this is advantageous as it allows communication with bodies while they freely behave.

In some embodiments, disclosed herein is a device system that can integrate with various types of neural interfaces that act as recording or stimulation electrodes, optical fibers, or as hollow tubes for media, e.g., fluid delivery. In still other embodiments, advantageous configurations for various treatment modalities including recording, stimulating, magnetic stimulation, magnetic monitoring, fluid delivery, temperature control, optical stimulation, optical monitoring, video monitoring, and chemical irrigation of neural tissue. In some embodiments, the systems and methods can be utilized to monitor nerve firing to locate nerves, such as parasympathetic, sympathetic, afferent, and/or efferent nerves prior to or during a denervation proceeding, such as renal denervation, a cardiac EP study, vagal nerve ablation, and the like.

In some embodiments, the device system can also serve as a delivery device for a drug, such as an antithrombotic agent, an antibiotic, an anti-inflammatory, an anti-epileptic, viral vectors, or a chemotherapeutic agent, for example. In some embodiments, the device system can be implanted within any tissue within the body dependent upon the desired research or clinical result; including nervous, muscle, connective, epithelial, cardiac, lung, renal, gastrointestinal, and bone tissues.

In some embodiments, the device system may include a neural interface to diagnosis and/or treat epilepsy, a movement disorder (e.g., Parkinson's Disease), a psychiatric disorder (e.g., clinical depression), the result of a stroke, Alzheimer's disease, a cognitive disorder, somatosensory disorder, an anxiety disorder, an eating disorder, an addition or craving, restless leg syndrome, a sleep disorder, Tourette's syndrome, a stress disorder, coma, autism, a hearing disorder, a vision disorder, blindness, retinal degeneration, age related macular degeneration, cortical injury, optic nerve injury, dry eye syndrome, a speech disorder, amblyopia, headaches, temporomandibular joint disorder, pain (e.g., phantom limb pain and chronic pain), urinary incontinence, erectile dysfunction, bone disease, arthritis, tendonitis, the result of ligament or tendon damage, and paralysis (e.g., facial nerve paralysis and spinal paralysis). In some embodiments, the implantable neural interface device can be used to provide motor control of a prosthetic such as a limb or an external computer. In still other embodiments, the implantable neural interface device can be used to provide sensation from a prosthetic such as a limb or an external computer.

In some embodiments, the device system may wirelessly communicate with a system that is connected to a network or cloud of data, or other storage device. In other embodiments, the device system is connected to a biological interface to monitor tissue. In some other embodiments, the device system is connected to a biological interface to modulate tissue. In still other embodiments, the device system is connected to a biological interface to monitor and modulate tissue. In other embodiments, the biological interface can include an implantable camera.

In other embodiments, the device system can include a biological interface to study, diagnose, and/or treat cardiovascular conditions such as heart failure, rheumatic heart disease, hypertensive heart disease, ischemic heart disease, angina, coronary artery disease, cerebral vascular disease, stroke, atherosclerosis, cerebrovascular disease, cardiomyopathy, pericardial disease, valvular heart disease, inflammatory heart disease, congenital heart disease, and peripheral arterial disease.

In still other embodiments, the device system can include a biological interface to study, diagnose, and/or treat cancers, including leukemia, lymphoma, myeloma, bladder cancer, lung cancer, brain cancer, melanoma, breast cancer, non-Hodgkin lymphoma, cervical cancer, and ovarian cancer.

In other embodiments, the device system can include a biological interface to study, diagnose, and/or treat type 1 and type 2 diabetes. In some embodiments, the device system can include a biological interface to study, diagnose, and/or treat orthopedic conditions, including osteoarthritis, rheumatoid arthritis, bone fractures, lower back pain, neck pain, and a herniated disk.

In other embodiments, the device system can include a biological interface to study, diagnose, and/or treat eye conditions, including glaucoma, cataracts, age-related macular degeneration, amblyopia, diabetic retinopathy, retinal detachment, retinal tearing, and dry eye syndrome.

In still other embodiments, the device system can include a biological interface to study, diagnose, and/or treat hearing conditions, including hearing loss, Meniere's disease, malformation of the inner ear, autoimmune inner ear disease, tinnitus, and vertigo.

In other embodiments, the device system can include a biological interface to study, diagnose, and/or treat tactile disorders, including impaired sensitivity to pressure applied to the skin, elevated two-point discrimination thresholds (i.e. impaired spatial acuity), loss of vibratory sense, and deficits in proprioception.

In other embodiments, the device system can include a biological interface to study, diagnose, and/or treat taste, taste impairing conditions, smell, and smell impairing conditions.

In still other embodiments, the implanted device system 100 can be movably positioned within the scalp, skin, muscle, bone, neural tissue, heart, lungs, trachea, bronchi, diaphragm, liver, pancreas, kidneys, bladder, urethra, spleen, esophagus, stomach, intestine, penis, testes, uterus, or ovary.

In some embodiments, provided is a closed loop control system for stimulating (or ablating) and monitoring neural activity. In some embodiments, systems and methods as disclosed herein can modulate neural tissue, and have a stimulatory or inhibitory effect. Neural tissue is specialized for the conduction of electrical impulses that convey information or instructions from one region of the body to another. About 98% of neural tissue is concentrated in the brain and spinal cord, which are the control centers for the nervous system. Neurons transmit signals as electrical charges which affect their cell membranes. A neuron has a cell body (soma) that contains a nucleus. The stimulus that results in the production of an electrical impulse usually affects the cell membrane of one of the dendrites, which then eventually travels along the length of an axon, which can be a meter long. Axons are often called nerve fibers with each ending at a synaptic terminal. Neuroglia are cells of the CNS (central nervous system) and PNS (peripheral nervous system) that support and protect the neurons. They provide the physical support for neural tissue by forming myelin sheaths, as well as maintaining the chemical composition of the tissue fluids and defending the tissue from infection. Schwann cells are specialized PNS cells that form myelin sheaths around neurons. Neurons (nerve cell) include a cell body that contains the nucleus and regulates the functioning of the neuron. Neurons also include axons that are cellular process (extension) that carry impulses away from the cell body. Neurons also include dendrites that are cellular process (extension) that carry impulses toward the cell body. A synapse is a space between axon of one neuron and the dendrite or cell body of the next neuron—transmits impulses from one neuron to the others. Neurotransmitters are chemicals released by axons and transmit impulses across synapses.

In still other embodiments, provided is a closed loop control system for stimulating and monitoring physiological activity. In other embodiments, systems and methods as disclosed herein can modulate tissue and organs, and have a stimulatory or inhibitory effect. A system could include a first antenna or pair of antennas configured for stimulation only, and a second antenna or pair of antennas configured for recording only. The first and second pair of antennas can operate at high data rates, and can advantageously obviate the need for large amounts of bidirectional communication from each individual antenna/pairs of antennas. The pair of antennas exclusively or substantially entirely dedicated to recording can send signals out of the body (or to another location within the body), while the pair of antennas exclusively or substantially entirely dedicated to stimulation can send signals to stimulate electrodes, end effectors delivering RF, microwave, electromagnetic, ultrasound, thermal, cryo, and/or other energy, fluid, etc. to antennas within the body or external to the body. Relegating the primary data stream of each pair to unidirectional only can allow for reduced overhead in wireless transmission, increasing the data rate available and a more robust closed loop control system for better control over the neural circuitry being modulated. This can advantageously allow for wireless closed loop control at high channel counts/data rates. In some embodiments, the system can be configured to record and/or stimulate about or at least about 100, 150, 250, 500, 1,000, 5,000, 10,000, 100,000, 500,000, 1,000,000 channels, or even more.

In some embodiments, microfilaments are used to record and stimulate neural tissue. In still other embodiments it is advantageous that the approximate diameter of circular microfilaments for conducting electrical current is between 1 µm and 250 µm, such as no more than about 25 µm, 50 µm, or 75 µm. For electrical stimulation, larger sites up to 50 µm would be advantageous to achieve surface areas that meet useful stimulation current requirements without a coating. The approximate diameter of circular microfilaments for conducting or monitoring light is between is 0.1 µm to 250 µm, such as no more than about 25 µm, 50 µm, or 75 µm. The approximate diameter of circular microfilament tubes for delivering or circulating gases, fluids, and mixtures in some embodiments is between 1 µm to 100 µm, or no more than about 50 µm, 75 µm, 100 µm, or 150 µm. Microfilaments can also be placed within a packed geometry that allows for a tapering of the penetrating area cross sections to reduce the cross sectional area and thus long term adverse neural tissue response. In some embodiments, the microfilaments can extend outward from the body's surface; these sites can be formed (e.g., bent or flattened) to provide desired functional characteristics.

A microfilament array body can take multiple forms including penetrating structures with microfilament sites and joining sections to optimize placement within the nervous system. An approximate cross sectional area of a penetrating array body in some embodiments is 1 $\mu m^2$ to 0.2 $mm^2$, preferably up to approximately 7850 $\mu m^2$. For large area coverage as in electrocorticography, larger body areas up to approximately 100 $cm^2$ or more would be advantageous to collect more data from the outer surface of a neural tissue section. Systems and methods as disclosed herein can be used or modified for use with neural arrays as disclosed, for example, in U.S. Pat. No. 9,095,267 to Halpern et al., which is hereby incorporated by reference in its entirety.

In some embodiments, the device system is movably assembled within a sealed connector assembly. In still other embodiments, the connector is movably assembled to another connector containing the wireless device system. In some embodiments, the wireless device system embedded in a connector assembly might be advantageous underwater, in corrosive environments, in low-visibility environments, in outer space, and in applications requiring a low force of connection. In other embodiments, the device system embedded within a wireless connector would be advantageous in blood, urine, hormones, and lymph. In still other embodiments, the device system would be advantageous in environments that limit the use of hands, including industrial, athletic, and military pursuits.

One advantage of an implantable wireless device in some embodiments is the wide range of materials and components available to improve implantation conditions and long term performance of a device within a nervous system. The components of the device can be formed from titanium, niobium, gold, platinum, platinum iridium, carbon, stainless steel, steel, aluminum, conductive polymers, polymers, ceramics, organic materials, combinations of the foregoing, or any other materials.

Various views of embodiments of a wireless device system 50 with some components implanted within the body is shown in FIG. 1. In general, two distinct parts of the device system can be distinguished: implant 100 and a second device 200, which may be an external device or another implanted device in some cases. In some embodiments, the implant has an array 120 of two, three, or more antennas. In some embodiments, some or all of the antennas within an array are surrounded by shielding 150. In still other embodiments, the external device 200 has an array of two or more antennas within a housing 240, surrounded by a shielding 250. In some embodiments, the implant antennas can transmit data to an external source, such as the external device 200 antennas configured to receive the transmitted data. In some embodiments, the external device 200 antennas can send data to another external device. In some embodiments, the devices are aligned using one, two, or more magnets. In still other embodiments, the magnetic attraction between device system 100 and device system 200 is strong enough to compress the thickness of tissue (shown between arrows 300) between them without causing discomfort or tissue compromise. In some embodiments, the tissue can be compressed by between about 0.05 mm and about 1 mm, such as between about 0.1 mm and about 0.5 mm. In some embodiments, use of pressure to reduce tissue thickness can also increase friction by forming a mechanical ledge with flexible skin. It is also be advantageous to improve transmission and avoid patients from having to shave hair—added pressure can flatten various hairstyles as much as possible.

In some embodiments, the implanted device is placed at a location beneath the scalp. In other embodiments, the implant is placed beneath the cranium. In still other embodiments, the bone is shaped to provide additional clearance for placement of the implant and increase the strength of wireless communication. In other embodiments, the device is placed within tissue at some location below the skull/cranium, such as, for example, deep to the skull, dura mater, arachnoid, pia mater, or bridging veins, and/or superficial to, or in between any of the foregoing structures. In some embodiments, the internal device can be placed on an endothelial, mesothelial, or adventitial layer of tissue, for example, or under or within the epidermis, dermis, or hypodermis of the skin.

In some embodiments, the device system includes a device with two or more antennas surrounded by shielding 150 that can allow antennas to operably communicate with antennas in other devices. In still other embodiments, the antennas communicate through covers 145 and 146 that are transparent or relatively transparent to electromagnetic radiation. In some other embodiments, the covers 145 and 146 are joined in a single cover. In still other embodiments, the joint cover formed from 145 and 146 wraps around the top edges of the implant device system 100 to allow wireless transmission in directions at angles that are not perpendicular to the cover (e.g., angle 305) such as at angles between 90° and 180°, such as no more than about 100°, 120°, 140°, 160° or 170°. In still other embodiments, an antenna operating at a different frequency is included in the device system to enable basic communication between devices at one frequency spectrum while another antenna communicates biological data at a different frequency spectrum. In other embodiments, one or more unshielded antennas can be operably connected to an antenna array of one or more shielded antennas. In still other embodiments, the shielding walls 155 and 255 surrounding antennas can be angled with respect to the horizontal plane (e.g., angle 258) at angles between, for example, 90° and 135°, such as no more than about 100°, 110°, 120°, or 130°, but greater than about 90° in some cases.

In some embodiments, the shielding also forms outer surfaces of the device systems 100 or 200. In still other embodiments, the device system 100 has shielding 150 that also acts as a portion of the hermetic assembly that can enable operation within the body. In some other embodiments, the shielding 150 is formed to encompass one, two, or more antennas and a single wall between two or more antennas. In still other embodiments, the shielding is formed that include channels that partially surround electrical connections to antennas. In some embodiments, some or all of the antennas can be coated with a material, such as a polymer for example.

In other embodiments, the device systems 100 or 200 include two or more operably independent shielded assemblies that are not physically connected. In still other embodiments, the device systems 100 or 200 can include two discrete operably independent shielded assemblies that are not physically connected, and placed adjacent one another.

In some embodiments, the antenna arrays communicate using Ultra-wideband. Ultra wideband uses low energy for short-range, high-bandwidth communications over a large portion of the radio spectrum. Ultra wide band can transmit information spread over a large bandwidth at levels equal to or greater than 500 MHz or 20% of fractional bandwidth. Ultra-wideband can be operable between 3.1 GHz and 10.6 GHz within plus or minus 0.1 GHz. In some embodiments, an antenna array can include two antennas and be configured for communication at a data rate between, for example, 1 kbps and 50 Gbps, such as no more than about 50 Mbps, 100 Mbps, 200 Mbps, 300 Mbps, 400 Mbps, 500 Mbps, 1 Gbps, 10 Gbps, 20 Gbps, 25 Gbps, 30 Gbps, or 40 Gbps. Ultra wide band can be advantageous within medical device applications because it transmits large amounts of data while requiring low levels of power, reducing the power requirements and maximum temperatures of implanted devices. In some embodiments, antennas within the device system are capable of operating, within plus or minus 5%, at frequencies between 6.765 MHz and 6.795 MHz, 13.553 MHz and 13.567 MHz, 26.957 MHz and 27.283 MHz, 40.66 MHz and 40.7 MHz, 433.05 MHz and 434.79 MHz, 902 MHz and 928 MHz, 24 GHz and 24.25 GHz, 61 GHz and 61.5 GHz, 122 GHz and 123 GHz, 244 GHz and 246 GHz, 401 MHz and 401.85 MHz, 401.85 MHz and 402 MHz, 402 MHz and 405 MHz, 405 MHz and 406 MHz, 413 MHz and 419 MHz, 426 MHz and 432 MHz, 438 MHz and 444 MHz, or 451 MHz and 457 MHz.

In some embodiments, the perimeter of the antennas can be rectilinear, circular, or irregularly shaped. In other embodiments, the antennas can be designed to be incapable of communication within a portion of the volume surrounding them within the housing(s). In some embodiments, an antenna can be positioned within the device system so that a zone of the surrounding volume incapable of communication is aligned with the zone of volume of another one or more antennas where communication is enabled, reducing interference between antennas. In some embodiments, antennas can be positioned such as the volume of overlap of a first volume (e.g., a first "dead zone") incapable of communication or attenuated communication of the first antenna with respect to a volume of overlap of a second volume incapable of communication or attenuated communication of the second antenna (e.g., a second "dead zone") is about or at least about 20%, 30%, 40%, 50%, 60%, 70%, 80%, 90%, or more. In still other embodiments, the portion of volumes of antennas incapable of communication and/or attenuated communication are aligned with tissue adjacent the device systems, reducing propagation of electromagnetic energy into the surrounding tissue and out of the body into the environment outside of the body and the wireless device system.

The performance of the wireless device system can be contributed to by many factors, including the positions of the antennas, shielding, and thickness of tissue between the arrays. In some embodiments, the antennas and shielding can be electronically configurable to operably perform across different thicknesses of tissue and frequency spectrums. In some embodiments, the shielding is a component of at least one antenna, and partially determines the frequency spectrum operably used. In other embodiments, the shielding is also an antenna operating on a different frequency spectrum than the array of antennas. In other embodiments, the walls 155 and 255 can be shaped with different angles, profiles, and thicknesses to adjust performance. In still other embodiments, the walls 155 and 255 can be dynamically adjusted, such as via actuators, to increase the device system's tolerance of misalignment. In some embodiments, the wall separating antennas can be between 1 μm and 5 mm, such as no more than 10 μm, 0.1 mm, 0.25 mm, 0.5 mm, 1 mm, 2 mm, 3 mm, or 4 mm in thickness. The device system can be capable of a misalignment that is a percentage of the shielding wall or distance between two antennas within an array, such as no more than 0.1%, 0.5%, 1%, 2%, 3%, 5%, 10%, 15%, 20%, 25%, 50%, 75%, 80%, 90%, or 100%.

In some embodiments, the sidewalls 155, 255 can extend axially distally a distance (shown as distance between arrows 310 in FIG. 1B) beyond that of the ends of the antennas, such as, for example, about 0.1 mm to about 10 mm, such as no more than about 0.25 mm, 0.3 mm, 0.5 mm, 1 mm, 3 mm, 5 mm, 7 mm, or 9 mm. In some embodiments, the air gap between the tops of the antennas and the shielding is an important aspect of boosting the antennas capability to communicate.

In some embodiments, wireless device systems 100 and 200 are assembled at a distance relative to one another that maintains a level of frequency spectrum leakage beyond the tissue and outside of the body and the wireless device system that is between −75 dBM/MHz and −41.3 dBM/MHz, such as no more than about −70 dBM/MHz, −60 dBM/MHz, or 50 dBM/MHz. In other embodiments, the shielding extends laterally beyond the antennas (e.g. dimension 320 in FIG. 1B) by a distance of between about 0.1 mm and about 10 mm, such as no more than about 0.5 mm, 0.75 mm, 1.0 mm, 2 mm, 5 mm, 7.5 mm, or 9 mm to contribute to maintaining a level of frequency spectrum leakage beyond the tissue and outside of the body and the wireless device system that is between −75 dBm/MHz and −41.3 dBm/MHz, such as no more than about −70 dBm/MHz, −60 dBm/MHz, or −50 dBm/MHz.

In some embodiments, comparing the communication between antennas can increase total device system performance and reliability. In some embodiments, comparing changes in frequency of communication between antennas would provide additional data contained within the total device communication performance. In some embodiments, comparing frequency, changes in frequency, amplitude, phase, pulse timing, or other modulation schemes between antennas can provide additional data contained within the total device communication performance. In other embodiments, the antennas can be designed to accept near field, far field, or a combination of near and far field radio frequency energy.

FIG. 1 shows a schematic view of a wireless device system 50, with an implanted device system 100 and a device system 200 outside of the body. A neural probe 110 for recording and simulation is part of the implanted device system 100. A wearable mount 210 is part of the external device system 200.

Figure 1A:
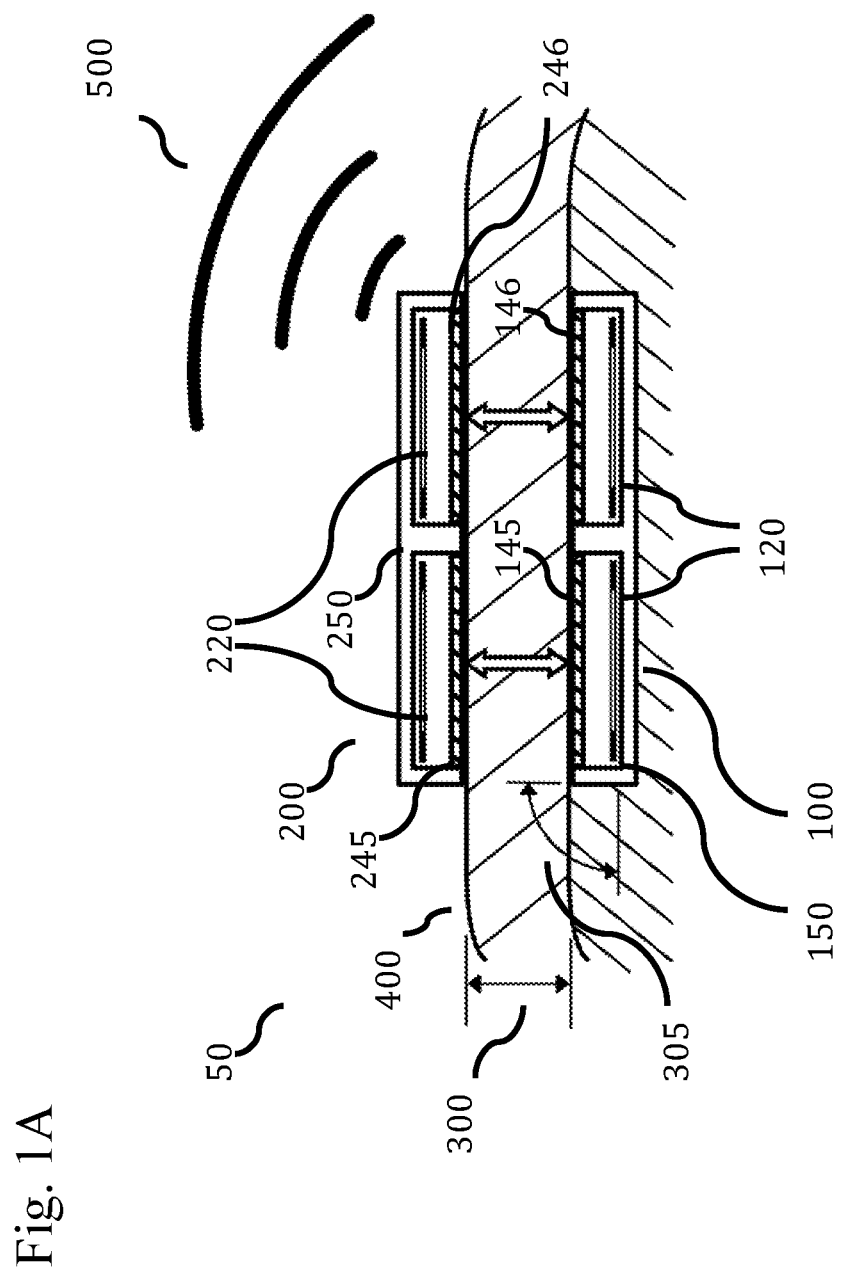
FIG. 1A shows the cross sections of an implanted device and an external device separated by tissue, according to some embodiments.

FIG. 1A illustrates a cross sectional view of a wireless device system 50 with tissue 400 between implanted device system 100 and a device system 200 outside of the body.

Antenna array 120 has shielding 150 surrounding its antennas. Antenna array 220 has shielding 250 surrounding its antennas. The housing covers 145, 146, 245, and 246 are transparent to electromagnetic radiation, allowing the two antenna arrays to operably communicate with each other in a bi-directional manner. A generic wireless symbol 500 symbolizes the potential of an external device system 200 to wirelessly communicate with other devices.

Figure 1B:
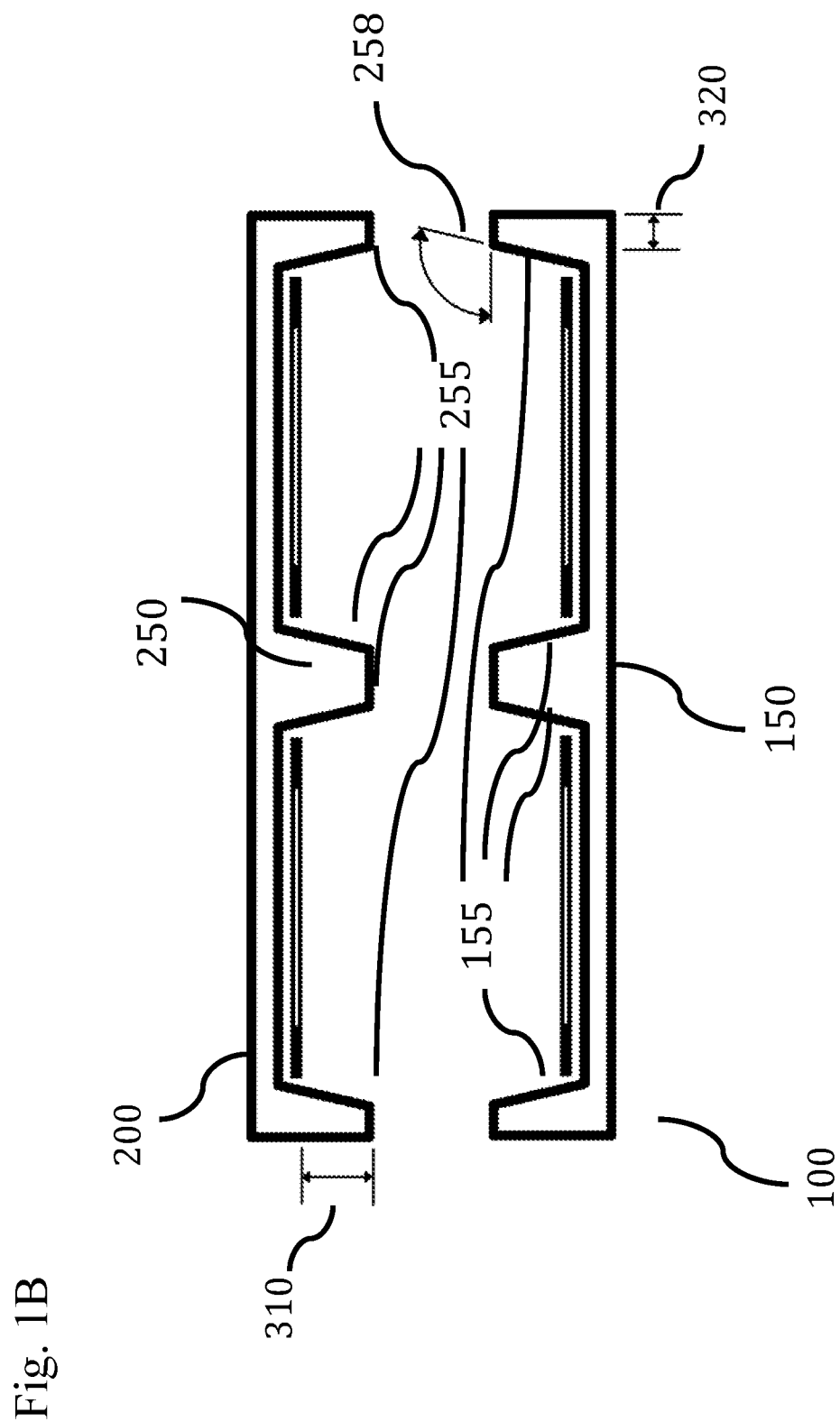
FIG. 1B shows block diagrams of the general componentry of an implanted device system and an external device system, according to some embodiments.

FIG. 1B illustrates cross sections of shielding for 150 and 250 with antennas in place. The walls 155 and 255 can be shaped with different angles, profiles, and thicknesses.

Figure 1C:
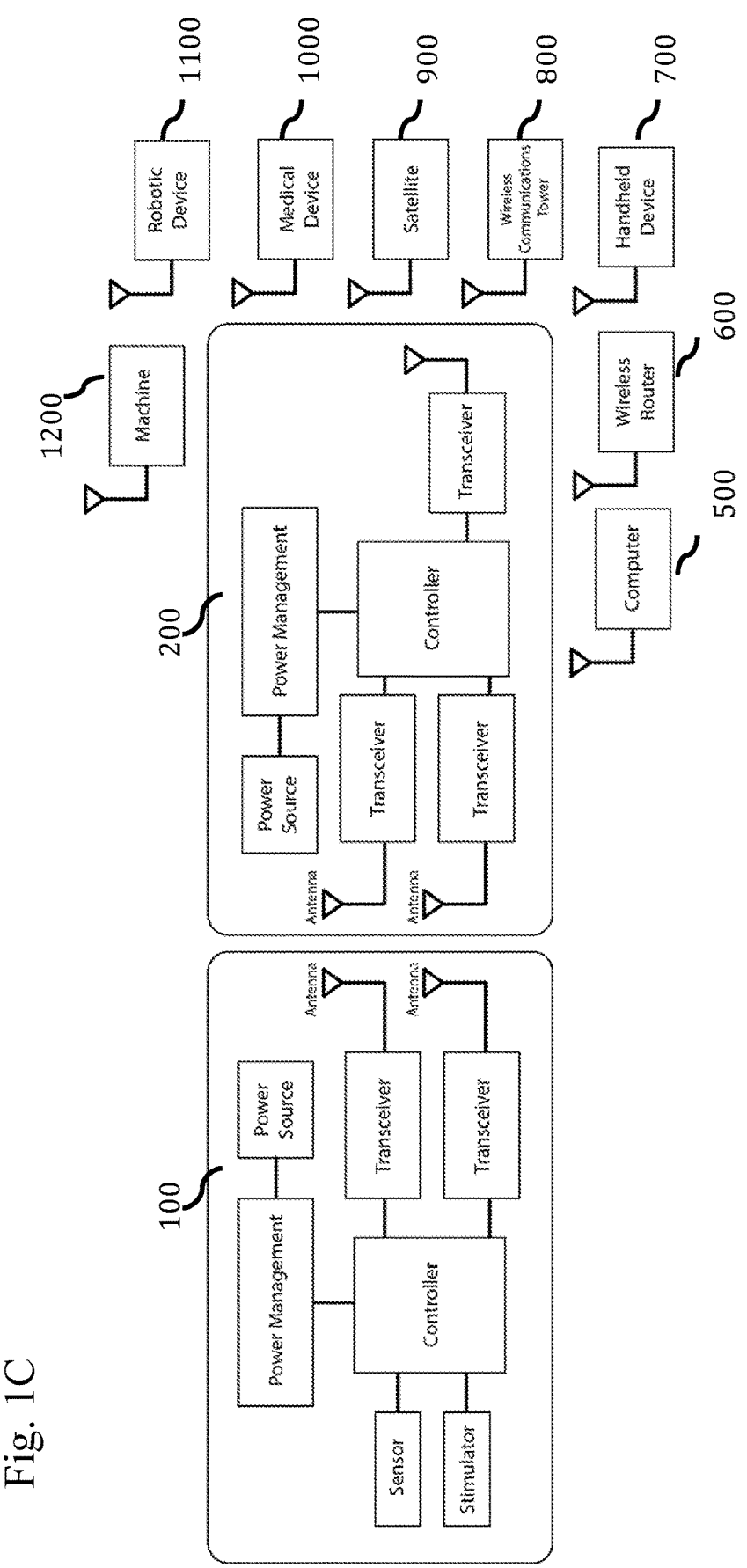
FIG. 1C illustrates a block diagram of a wireless device system, according to some embodiments.

FIG. 1C illustrates a block diagram of a wireless device system. The device 200 can operably wirelessly communicate with devices including a computer 500, a wireless router 600, a hand held device 700, a wireless communication tower 800, a satellite 900, a medical device 1000, a robotic device 1100, and a machine 1200.

Also disclosed herein in some embodiments are systems and methods for data compression. As channel counts increase, wireless neural interfaces require higher data rates to communicate signals into and out of the body. Methods for transmitting channel location data, include one bit per channel and a unique channel address that includes a set pre-determined number of bits. When the number of channels within a neural interface increases to, for example, over one thousand channels, the addressing of every channel increases the required data rate significantly. The data rate continues to increase significantly as the number of neural interface channels increases beyond one hundred thousand channels and beyond one million channels.

However, only a small percentage of neurons fire at any given time within sections of the nervous system. The important information a wireless neural interface communicates is, for example, the location of firing neurons or the location of neurons to be stimulated to fire. To reduce the total data rate required for high numbers of channels, it would be advantageous to communicate only the locations of firing neurons or neurons to be stimulated to fire.

Figure 2:
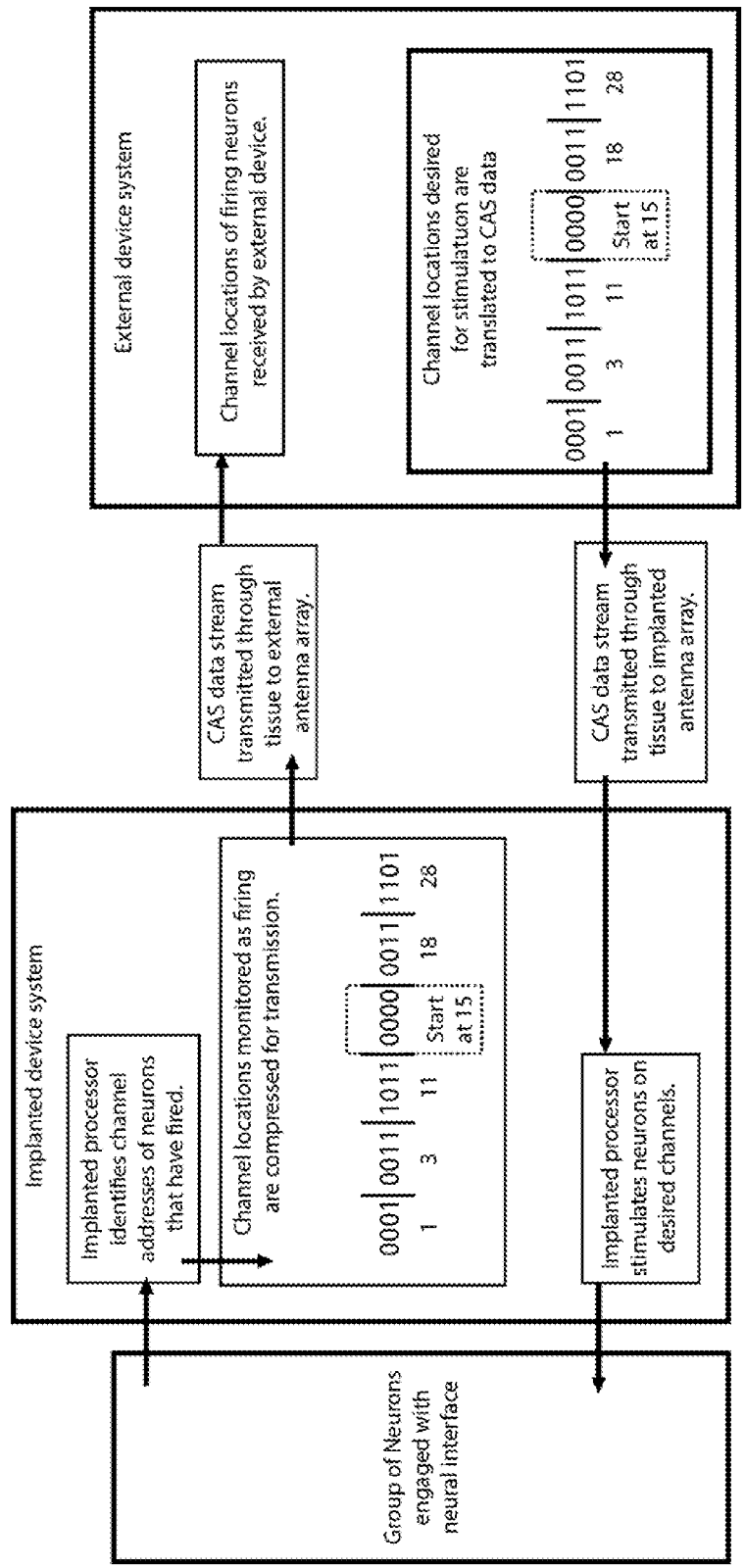
FIG. 2 illustrates schematically a neural data compression system, according to some embodiments.

FIG. 2 illustrates the compression of channels 1, 3, 11, 18, and 28 to a total bit size of 24 bits. A 1 bit per channel scheme would require 32 bits, and a unique channel address scheme would require 25 bits. In FIG. 2, the data compression uses the 4 bit designation (also referred to herein as a starter marker code) "0000" to signify a starting point of 15 for compressing channel addresses higher than 14. In FIG. 2, the 4 bits of "0000" are inserted after "1011" (i.e. channel 11) signifying a new starting point of 15 (the highest potential value of the 4 bit channel). The next 4 bits inserted are "0011" (i.e., 3), 3 is added to 15, to encode the channel 18. Larger steps to new starting points can be taken by repeating the "0000" 4 bit designation more than once; two consecutive "0000" designations signify a starting point of 30, and so on. In some embodiments, a system could use "0001" in addition to "0000". 0001 could mean a starting point of 100 while 0000 still means a starting point of 15. As such, a plurality of starter marker codes having the same and/or different number of pre-selected bits can be utilized.

This described data compression system and method advantageously provides a compact, and lossless means from relaying sparse data in real time from a large, streaming dataset. The described data compression increases in effectiveness as the number of channels increases within a neural interface. The described data compression also increases in effectiveness as the frequency of sampling the channels increases.

In some embodiments, the wireless device system uses data compression to reduce the data rate required to communicate neuron firing events or commands. In still other embodiments, the data compression reduces data rate by communicating a percentage of the total channels contained within a neural interface, at percentages between 1% and 50% such as no more than about 5%, 10%, 15%, 20%, 25%, 30%, or 40%.

In other embodiments, the data compression can be interlaced with additional data. In still other embodiments, the data compression can be interlaced with additional data associated with channel addresses.

In some other embodiments, multiple designations can be used to indicate a range of starting points for the address data that follows. In still other embodiments, the number of bits used for the designation of a new starting point for addresses can be operably adjusted either higher, lower, or both depending on the amount of data and/or the neural circuitry.

FIG. 2 shows a flow diagram that describes the use of data compression to reduce the total data rate required to communicate neuron firing events or commands for neurons to fire on specific channels. As shown in the non-limiting example, Channels 1, 3, 11, 18, and 28 are shown as the locations of firing events, and the locations of neurons to be stimulated to fire.

In other words, in some embodiments, disclosed herein is a method of transmitting compressed data from a location within or external to the body to a location internal or external to the body. The method can include, for example, receiving data from a plurality of channels relating to activity within the body (or in some cases sending data corresponding to stimulation or ablation commands for a plurality of channels); filtering data from the channels correlating to a subset of activity; encoding the filtered data from the subset of channels into a first set of subaddresses comprising a pre-selected number of bits, each subaddress corresponding to an individual channel of the subset of channels; and transmitting the encoded, filtered data to a receiver at the location external to or internal to the body. Encoding the data from the subset of channels can include creating a second subset of subaddresses comprising starter marker codes not directly relating to the identity of an individual channel. The method can also include decoding the encoded, filtered data. Decoding can include processing the first set of subaddresses and the second set of subaddresses to determine the identity of each individual channel of the subset of channels. In some embodiments, encoding can include dynamically varying either more or less the pre-selected number of bits of the starter marker codes depending on the amount of data received. In some embodiments, the starter marker codes comprise bits all having zeroes, or other configurations. In some embodiments, the systems can include 2, 3, 4, 5 or more distinct starter marker codes having the same or different number of pre-selected bits, such as 4, 5, 6, 7, 8, 9, 10, 20, 30, 40, 50, 100, 200, 300, 400, 500, or more bits. The subset of activity within the body can include, for example, firing neurons, such as about or at least about 10, 20, 30, 40, 50, 60, 70, 80, 90, 100, 1,000, 10,000, 100,000, or even more. The subset of activity can also include pixels, such as calcium ion monitoring. Sodium, chloride, potassium, and other channels can be monitored as well. In some embodiments, the subset of activity includes stimulation/ablation/other commands for a number of channels associated with various neurons/selected areas of the body for treatment. Encoding the filtered data can include compressing the filtered data by about or at least about 10%, 20%, 30%, 40%, 50%, or more. In some embodiments, the starter marker codes comprise a plurality of distinct binary codes having the same or different number of pre-selected bits. In some embodiments, a system for transmitting compressed data from a first location to a second location internal to the body can include a processor configured to receive data from a plurality of channels relating to stimulation commands within the body; filter data from the channels correlating to a subset of activity relating to the stimulation commands within the body; and encode the filtered data from the subset of channels into a first set of subaddresses comprising a pre-selected number of bits, each subaddress corresponding to an individual channel of the subset of channels. The system can also include at least one antenna configured to transmit the encoded, filtered data to a receiver at the location internal to the body. The processor can be further configured to encode the data from the subset of channels by creating a second subset of subaddresses comprising starter marker codes not directly relating to the identity of an individual channel. In some embodiments, another advantage of data compression beyond reducing wireless data rates and associated power consumption is increasing the effective storage capacity on internal and/or external memory storage (e.g., hard drives, flash memory, etc.).

Also disclosed herein is a system for transmitting compressed data from a location within the body or external to the body to a location internal to or external to the body. In some embodiments, the system can include electrode(s) implanted in the brain and an autonomous wireless controller implanted beneath the scalp or in another location. Transmission can be "incoming," that is data corresponding to, for example, commands to stimulate or ablate at discrete locations within the body. Transmission can also be "outgoing," to record activity within the body. Transmission can also be bi-directional as part of a closed loop feedback system. The system can include, for example, a processor configured to receive data from a plurality of channels relating to activity within the body; filter data from a subset of channels correlating to a subset of activity within the body; and encode the filtered data from the subset of channels into a first set of subaddresses comprising a pre-selected number of bits, each subaddress corresponding to an individual channel of the subset of channels; and at least one antenna configured to transmit the encoded, filtered data to a receiver at the location external to the body. The processor can be further configured to encode the data from the subset of channels by creating a second subset of subaddresses comprising starter marker codes not directly relating to the identity of an individual channel. A predetermined starter marker code, such as, for example, one, two, or more repeating "0000" data sub-addresses having the predetermined length of bits directly can signify a new starting point for data having an absolute value greater than that could be expressed with the previous sequences of bits having the predetermined length. The starter marker code can signify that the next the next encoded data corresponding to a channel address corresponds to the sum of (1) the maximum possible value of the null marker channel plus (2) the absolute value of the non-null data address sequence. The maximum possible value of the starter marker could be in some cases $2^n-1$, wherein n is the predetermined length bit of each channel. A processor can be configured to distinguish between the actual encoded data corresponding to each individual channel and particularly identify each starter marker code, and perform the necessary aforementioned calculation to determine the actual channel addresses of each firing neuron.

Figure 3:
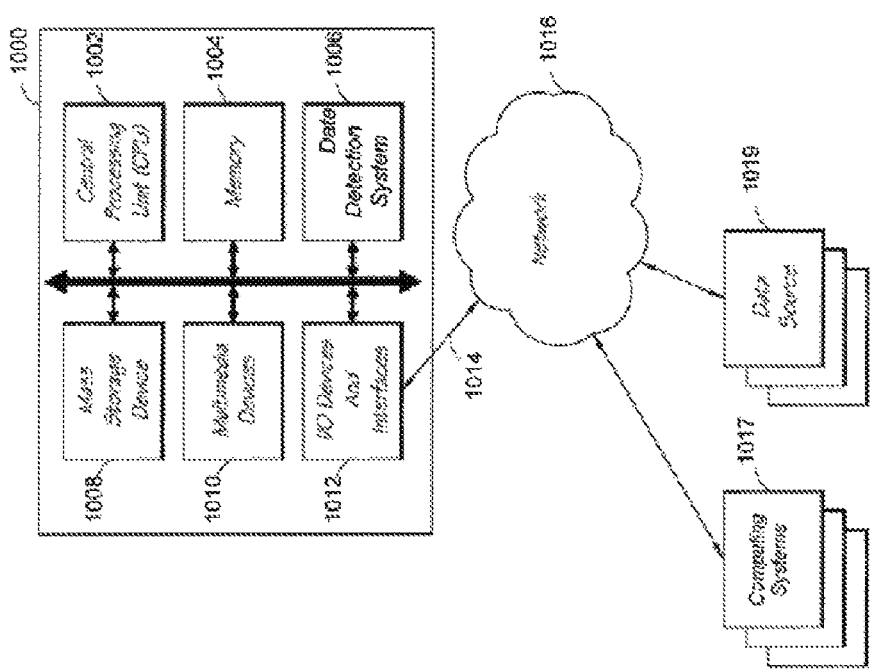
FIG. 3 illustrates a computer system that can be configured for use with a wireless neural data system, according to some embodiments.

FIG. 3 is a block diagram depicting an embodiment of a computer hardware system configured to run software for implementing one or more embodiments of the systems described herein.

In some embodiments, the computer devices, clients, and/or servers described herein take the form of a computing system 1000 illustrated in FIG. 10 which is a block diagram of one embodiment of a computing system that is in communication with one or more computing systems 1017 and/or one or more data sources 1019 via one or more networks 1016. The computing system 1000 may be used to implement one or more of the systems and methods described herein. In addition, in one embodiment, the computing system 1000 may be configured to manage access or administer a software application. While FIG. 3 illustrates one embodiment of a computing system 1000, it is recognized that the functionality provided for in the components and modules of computing system 1000 may be combined into fewer components and modules or further separated into additional components and modules.

In one embodiment, the computing system 1000 comprises an encoding and/or decoding module 1006 that carries out the functions described herein with reference to detecting and/or processing data, including any one of the techniques described above. The data detection system module 1006 and/or other modules or functional units disclosed herein may be executed on the computing system 1000 by a central processing unit 1002 discussed further below.

In general, the word "module," as used herein, refers to logic embodied in hardware or firmware, or to a collection of software instructions, possibly having entry and exit points, written in a programming language, such as, for example, COBOL, CICS, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

In one embodiment, the computing system 1000 also comprises a mainframe computer suitable for controlling and/or communicating with large databases, performing high volume transaction processing, and generating reports from large databases. The computing system 1000 also comprises a central processing unit ("CPU") 1002, which may comprise a conventional microprocessor. The computing system 1000 further comprises a memory 1004, such as random access memory ("RAM") for temporary storage of information and/or a read only memory ("ROM") for permanent storage of information, and a mass storage device 1008, such as a hard drive, diskette, or optical media storage device. Typically, the modules of the computing system 1000 are connected to the computer using a standards based bus system. In different embodiments, the standards based bus system could be Peripheral Component Interconnect (PCI), Microchannel, SCSI, Industrial Standard Architecture (ISA), and Extended ISA (EISA) architectures, for example.

The computing system 1000 comprises one or more commonly available input/output (I/O) devices and interfaces 1012, such as a keyboard, mouse, touchpad, and printer. In one embodiment, the I/O devices and interfaces 1012 comprise one or more display devices, such as a monitor, that allows the visual presentation of data to a user. More particularly, a display device provides for the presentation of GUIs, application software data, and multimedia presentations, for example. In one or more embodiments, the I/O devices and interfaces 1012 comprise a microphone and/or motion sensor that allow a user to generate input to the computing system 1000 using sounds, voice, motion, gestures, or the like. In the embodiment of FIG. 10, the I/O devices and interfaces 1012 also provide a communications interface to various external devices. The computing system 1000 may also comprise one or more multimedia devices 1010, such as speakers, video cards, graphics accelerators, and microphones, for example.

The computing system 1000 may run on a variety of computing devices, such as, for example, a server, a Windows server, a Structure Query Language server, a Unix server, a personal computer, a mainframe computer, a laptop computer, a tablet computer, a cell phone, a smartphone, a personal digital assistant, a kiosk, an audio player, an e-reader device, and so forth. The computing system 1000 is generally controlled and coordinated by operating system software, such as z/OS, Windows 95, Windows 98, Windows NT, Windows 2000, Windows XP, Windows Vista, Windows 10, Windows 8, Linux, BSD, SunOS, Solaris, Android, iOS, BlackBerry OS, or other compatible operating systems. In Macintosh systems, the operating system may be any available operating system, such as MAC OS X. In other embodiments, the computing system 1000 may be controlled by a proprietary operating system. Conventional operating systems control and schedule computer processes for execution, perform memory management, provide file system, networking, and I/O services, and provide a user interface, such as a graphical user interface ("GUI"), among other things.

In the embodiment of FIG. 3, the computing system 1000 is coupled to a network 1016, such as a LAN, WAN, or the Internet, for example, via a wired, wireless, or combination of wired and wireless, communication link 1014. The network 1016 communicates with various computing devices and/or other electronic devices via wired or wireless communication links. In the embodiment of FIG. 3, the network 1016 is communicating with one or more computing systems 1017 and/or one or more data sources 1019.

Access to the data detection system module 1006 of the computer system 1000 by computing systems 1017 and/or by data sources 1019 may be through a web-enabled user access point such as the computing systems' 1017 or data source's 1019 personal computer, cellular phone, smartphone, laptop, tablet computer, e-reader device, audio player, or other device capable of connecting to the network 1016. Such a device may have a browser module that is implemented as a module that uses text, graphics, audio, video, and other media to present data and to allow interaction with data via the network 1016.

The browser module may be implemented as a combination of an all points addressable display such as a cathode-ray tube (CRT), a liquid crystal display (LCD), a plasma display, or other types and/or combinations of displays. In addition, the browser module may be implemented to communicate with input devices 1012 and may also comprise software with the appropriate interfaces which allow a user to access data through the use of stylized screen elements such as, for example, menus, windows, dialog boxes, toolbars, and controls (for example, radio buttons, check boxes, sliding scales, and so forth). Furthermore, the browser module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition a touch screen may act as a hybrid input/output device. In another embodiment, a user may interact with the system more directly such as through a system terminal connected to the score generator without communications over the Internet, a WAN, or LAN, or similar network.

In some embodiments, the system 1000 may comprise a physical or logical connection established between a remote microprocessor and a mainframe host computer for the express purpose of uploading, downloading, or viewing interactive data and databases on-line in real time. The remote microprocessor may be operated by an entity operating the computer system 1000, including the client server systems or the main server system, an/or may be operated by one or more of the data sources 1019 and/or one or more of the computing systems 1017. In some embodiments, terminal emulation software may be used on the microprocessor for participating in the micro-mainframe link.

In some embodiments, computing systems 1017 who are internal to an entity operating the computer system 1000 may access the data detection system module 1006 internally as an application or process run by the CPU 1002.

In an embodiment, a user access point or user interface comprises a personal computer, a laptop computer, a tablet computer, an e-reader device, a cellular phone, a smartphone, a GPS system, a Blackberry® device, a portable computing device, a server, a computer workstation, a local area network of individual computers, an interactive kiosk, a personal digital assistant, an interactive wireless communications device, a handheld computer, an embedded computing device, an audio player, a smartphone, a smartwatch, or the like.

In addition to the systems that are illustrated in FIG. 10, the network 1016 may communicate with other data sources or other computing devices. The computing system 1000 may also comprise one or more internal and/or external data sources. In some embodiments, one or more of the data repositories and the data sources may be implemented using a relational database, such as DB2, Sybase, Oracle, CodeBase and Microsoft® SQL Server as well as other types of databases such as, for example, a flat file database, an entity-relationship database, and object-oriented database, and/or a record-based database.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A neural interface, comprising:
a housing configured to be implanted at a location in a patient under a skull and proximate neural tissue, the housing having a longitudinal axis;
a first antenna within the housing and configured to transmit neural data wirelessly to an external device;
a second antenna within the housing and configured to transmit neural data wirelessly to the external device,
wherein the first antenna and the second antenna transmit the neural data on the same or an overlapping frequency spectrum,
wherein the housing comprises shielding partially surrounding the first antenna and second antenna,
wherein the housing comprises one or more shielding-free windows, each shielding-free window comprising a window axis parallel to the longitudinal axis of the housing, the shielding-free windows configured to allow the first antenna and the second antenna to allow wireless transmission at angles between perpendicular to the window axis and aligned with the window axis.

2. The neural interface of claim 1, further comprising a third antenna, wherein the third antenna is unshielded, wherein the third antenna transmits data on a frequency spectrum different from that of the first antenna and the second antenna.

3. The neural interface of claim 1, wherein the first antenna and the second antenna are spaced apart and separated by a wall.

4. The neural interface of claim 3, wherein the wall is dynamically movable.

5. The neural interface of claim 1, wherein the shielding extends laterally beyond the first antenna and the second antenna.

6. The neural interface of claim 5, wherein the shielding extends laterally by a distance of between about 0.1 mm and about 10 mm.

7. The neural interface of claim 1, further comprising an air gap between the one or more windows and the antennas.

8. The neural interface of claim 1, wherein the first antenna and the second antenna transmit the neural data via an ultra-wideband protocol.

9. The neural interface of claim 1, further comprising a third antenna and a fourth antenna forming a pair of antennas, wherein the first antenna and the second antenna are configured to record data, and the third and fourth antennas are configured to send or receive stimulation commands, wherein the first, second, third, and fourth antennas are part of a closed-loop control system.

10. The neural interface of claim 1, comprising a first antenna array and a second antenna array, wherein the housing further comprises a processor configured to compare the frequency and/or modulation of a signal of communication of the first antenna array and the second antenna array.

11. The neural interface of claim 1, wherein the first antenna and the second antenna are oriented such that the first antenna comprises a first dead zone comprising a first non-transmissible or attenuated volume within the housing and the second antenna comprises a second dead zone comprising a second non-transmissible or attenuated volume within the housing, wherein the first volume and the second volume overlap by at least about 50%.

12. A neural interface, comprising:
a housing configured to be implanted at a location in a patient under a skull and proximate neural tissue, the housing having a longitudinal axis;
a first antenna within the housing and configured to transmit data wirelessly;
a second antenna within the housing and configured to transmit data wirelessly,
wherein the housing comprises shielding partially surrounding the first antenna and second antenna,
wherein the housing comprises one or more windows, each window comprising a window axis parallel to the longitudinal axis of the housing, the one or more windows configure to allow the first antenna and the second antenna to allow wireless transmission at angles between perpendicular to the window axis and aligned with the window axis.

13. The neural interface of claim 12, further comprising a third antenna.

14. The neural interface of claim 13, wherein the third antenna transmits data on a frequency spectrum different from that of the first antenna and the second antenna.

15. The neural interface of claim 13, wherein the third antenna is unshielded.

16. The neural interface of claim 12, wherein the first antenna and the second antenna are spaced apart.

17. The neural interface of claim 12, wherein the shielding extends laterally beyond the first antenna and the second antenna.

18. The neural interface of claim 12, wherein the first antenna and the second antenna transmit the neural data via an ultra-wideband protocol.

19. The neural interface of claim 12, wherein the first antenna and the second antenna are configured to record data.

20. The neural interface of claim 12, wherein the housing further comprises a processor.

* * * * *